United States Patent [19]
Harnoncourt et al.

[11] Patent Number: 5,503,151
[45] Date of Patent: Apr. 2, 1996

[54] APPARATUS FOR MEASURING THE PARAMETERS OF RESPIRATORY GASES

[75] Inventors: Karl Harnoncourt, Graz, Austria; Walter Guggenbuhl, Stafa, Switzerland; Rolf M. Schlegelmilch, Wurzburg, Germany; Christian Buess, Zurich, Switzerland

[73] Assignee: NDD Medzintechnik GmbH, Wurzburg, Germany

[21] Appl. No.: 301,252

[22] Filed: Sep. 6, 1994

[30] Foreign Application Priority Data

Sep. 30, 1993 [DE] Germany .......................... 43 33 410.5
Mar. 21, 1994 [DE] Germany .......................... 44 09 589.9

[51] Int. Cl.⁶ .............................. A61B 8/00; A61B 5/087
[52] U.S. Cl. ..................... 128/660.02; 128/719; 128/725
[58] Field of Search ................... 128/719, 725, 128/724, 721, 660.01, 660.02, 661.07

[56] References Cited

U.S. PATENT DOCUMENTS

| | | | |
|---|---|---|---|
| 3,903,742 | 9/1975 | Colton | 128/725 X |
| 3,927,670 | 12/1975 | Turney et al. | 128/725 |
| 4,206,763 | 6/1980 | Pedersen | 128/660.09 |
| 4,252,125 | 2/1981 | Iinuma | 128/660.08 |
| 4,341,222 | 6/1982 | Gardineer et al. | 128/660.01 |
| 4,347,850 | 9/1982 | Kelly-Fry et al. | 128/660.01 |
| 4,545,385 | 10/1985 | Pirschel | 128/660.09 |
| 4,657,021 | 4/1987 | Perry | 128/630 |
| 4,873,982 | 10/1989 | Morrison | 128/630 |
| 4,917,096 | 4/1990 | Engelhart et al. | 128/660.1 |
| 5,277,070 | 1/1994 | Dorr | 73/861.28 |
| 5,287,851 | 2/1994 | Beron et al. | 128/725 X |
| 5,383,470 | 1/1995 | Kolbly | 128/725 |

OTHER PUBLICATIONS

European Pat Appln 0 051 293 Published Dec. 5, 1982 to Ogura et al.
Plant, D. I. et al "Design of UTS Pneumotachometer", IEEE BME Trans. vol. BME-27 No. 10 Oct. 1980.
Blumenfeld, W. et al "A Coax UTS Pneumotachometer", MBE vol. 13 No. 6 pp. 855–860 Nov. 1975.

*Primary Examiner*—Francis Jaworski
*Attorney, Agent, or Firm*—Morgan & Finnegan

[57] ABSTRACT

The invention relates to an apparatus for measuring the parameters of respiratory gases comprising a respiratory tube, ultrasonic sensors and pre-amplifier electronic circuitry arranged in a separate housing. In order to prevent dangerous cross infections between patients following repeated utilization of the such measuring apparatus the ultrasonic sensors are permanently integrated in the respiratory tube so that they constitute a single part therewith and in that at least the respiratory tube together with the integrated ultrasonic sensors is designed in the form of an interchangeable part for use once only.

13 Claims, 1 Drawing Sheet

APPARATUS FOR MEASURING THE PARAMETERS OF RESPIRATORY GASES

FIELD OF THE INVENTION

The invention relates to an apparatus for measuring the parameters of respiratory gases comprising a respiratory tube and ultrasonic sensors and pre-amplifier electronic circuitry which is arranged in a separate housing.

BACKGROUND OF THE INVENTION

Conventionally at the present time discrete sensors are employed for measuring flow and the composition of respiratory gases, and furthermore other quantities such as for instance pressure, more particularly in intensive care and anesthesia and also in general medical diagnostics. The flow of respiratory gas is measured using various different techniques as for example by a pneumotachograph or by means of anemometry at a respiratory tube or in a respirator. The different gas concentrations of respiratory gas are determined, in a manner independent thereof, predominantly in the shunt or, partly, in the main flow using different principles, for example by infrared spectroscopy, paramagnetism or mass spectroscopy. The gas pressure in the respiratory passages is again separately measured at the mouth or in the respirator. Owing to the different measuring arrangements delays in time occur between the individual signals for the measured values, In most cases the signals are not measured directly at the mouth, but at other positions so that it is difficult to see the timing thereof in relation to the breathing of the patient, In the case of gas determination in the shunt flow there are furthermore transients, which are responsible for errors in the accuracy of measurement. Moreover, the methods are frequently intricate and expensive when employed in combination.

As employed in hospitals such measuring equipment is involved in the treatment of several patients each day so that there is the danger of cross infections between them.

One object of the present invention is consequently the provision of an apparatus for the measurement of respiratory gas parameters in accordance with the preamble of claim 1, in the case of the respiratory gas parameters are simultaneously measured.

SUMMARY OF THE INVENTION

In order to achieve this aim, starting with a measuring apparatus of the type initially mentioned, the invention contemplates the use of the measures in accordance with the characterizing part of claim 1 herein. In accordance with this, in a measuring apparatus comprising a respiratory tube, ultrasonic sensors and pre-amplifier electronic circuitry arranged in a separate housing, the ultrasonic sensors are permanently integrated in the respiratory tube so that they constitute a single-element part therewith. In this respect it is possible for the ultrasonic sensors to be cast in corresponding heads of the respiratory tube. Together with the integrated ultrasonic sensors the respiratory tube constitutes an interchangeable part for use once only, which is adapted to be inserted into the mouth of the patient using a mask or a respiratory tube. The respiratory tube may, in special cases, be gas-sterilized and used again.

It is furthermore possible to integrate a pressure sensor in the respiratory tube, preferably by casting.

The respective electronic module is then to be so designed that the pressure value detected is also processed.

It is furthermore possible for an infrared light source to be permanently integrated in the respiratory tube and arranged opposite to an optical sensor. It is by means of such sensing system that $CO_2$, $N_2O$ and other gases utilized in anesthesia may be determined using infrared absorption methods. The infrared light source may also be arranged adjacent to the optical sensor, if the wall, opposite to the sensor, of the respiratory tube is given a mirror finish and such a configuration that the light emitted by the light source is reflected there and can be received by the pickup. In the case of this embodiment of the invention it is furthermore possible for the optical sensor to be permanently installed in the electronic circuitry housing. This renders possible a particularly compact design.

DETAILED DESCRIPTION OF THE INVENTION

The respiratory tube may with advantage be manufactured of a transparent material and more particularly of a medicinal quality polymer transparent to light. In this case the light source and the optical sensor may be integrally cast in the wall of the respiratory tube, since the radiation is able to pass through the wall. Both the light source and also the sensor are also connected with the electronic circuitry so that they are on the one hand supplied with power and on the other hand the signals may be supplied for further processing.

It is a particular advantage if that infrared light source and the associated optical sensor are so installed adjacent to the ultrasonic sensor transversely in relation to the course of the respiratory tube that the connecting lines between the ultrasonic sensors and the connecting lines between the infrared light source and the associated ultrasonic sensor intersect with each other. This opens up the possibility of having a particularly compact design with little dead space.

The infrared light source and the associated optical sensor may also be adapted to be mounted on the respiratory tube using a plug-on holder and be connected with the same. Accordingly it is possible for the infrared light source and the associated optical sensor to be employed more than once, if the respiratory tube is replaced. Neither the infrared light source nor the optical sensor come contact with the respiratory gas flowing through the respiratory tube.

In the housing for the electronic circuitry it is possible for an light source to be installed, which emits suitable light, which penetrates the wall of the respiratory tube and impinges on a suitable fluorescent dye applied thereon. Adjacent to the light source it is possible to arrange an optical pickup in the housing for the electronic circuitry, which by luminescence or fluorescence measurements determines the oxygen concentration. In this respect it is possible for the wall of the respiratory tube to be configured in a suitable manner in order to ensure an improved conduction or guidance of light.

In accordance with one embodiment of the invention the housing for the pre-amplifier electronic system is adapted to be flange mounted on the respiratory tube, the conduction of the power supply and of the signals to the sensors integrated in the housing taking place via an encoded plug-in board. The flange mounted electronic circuitry housing will not come into contact with the respiratory flow of the patient and may accordingly be reused. In the housing for the pre-amplifier electronic system it is possible for further connections to be present for data lines, as for instance for the data from a separately connected $O_2$ analyzer. If an $O_2$ analyzer with a signal output is provided, it is possible for the signal for the $O_2$ composition to be supplied to the electronic circuitry of the respiratory tube. The $CO_2$ concentration may be exactly determined by way of the mol mass and $O_2$ concentration.

In accordance with a still further development of the invention it is possible for the pre-amplifier electronic system also to be cast directly in the floor of the respiratory tube.

Finally it is possible for the respiratory tube as a whole to be so dimensioned that it fits the mask and respirator tube connections employed in equipment for infants. Accordingly the respiratory tube may also be employed in pediatrics and neonatology.

The invention therefore contemplates the provision of a respiratory tube for use once over or for multiple use after gas sterilization, which is plug fitted to a mask or to a tube directly in front of the mouth of the patient. The respiratory tube renders possible measurement of flow rate of respiratory gases and of the mol mass, the concentration of one or more gases and of the proximal respiratory passage. Natural or artificial respiration of the patient is not hindered or interfered with by the measuring arrangement, since the measurement takes place in the free cross section of the tube. Parts of the sensor system, more particularly the ultrasonic sensors and the pressure transducer, are directly included in the respiratory tube as parts thereof. Other parts of the sensor system, which are designed in the form of optical pickups, are also included in the respiratory tube or are flange mounted thereon.

From the primary parameters measured using the apparatus in accordance with the invention it is possible for derived quantities, such as for example oxygen uptake, $CO_2$ release, the respiratory quotient, the vital capacity, the respiratory volumetric flow rate, the respiratory work and the like, to be calculated.

Further advantageous developments and convenient forms of the invention will be understood from the embodiment thereof illustrated in the accompanying drawings.

DETAILED DESCRIPTION OF THE FIGURES

Figure 1:
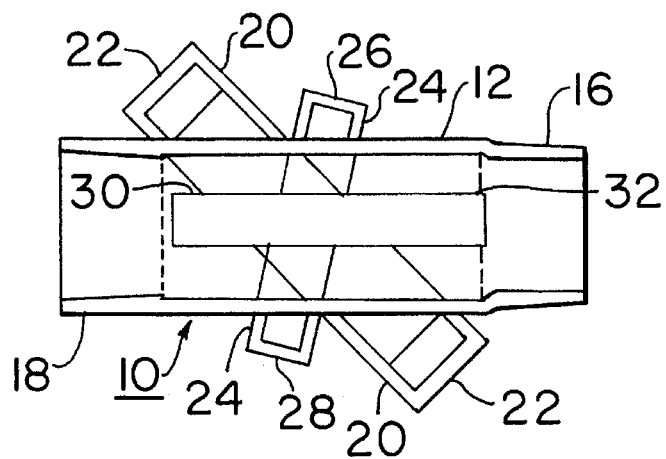
FIGS. 1 through 3 thereof show three different sectional representations of a respiratory tube in accordance with an embodiment of the present invention.
Figure 2:
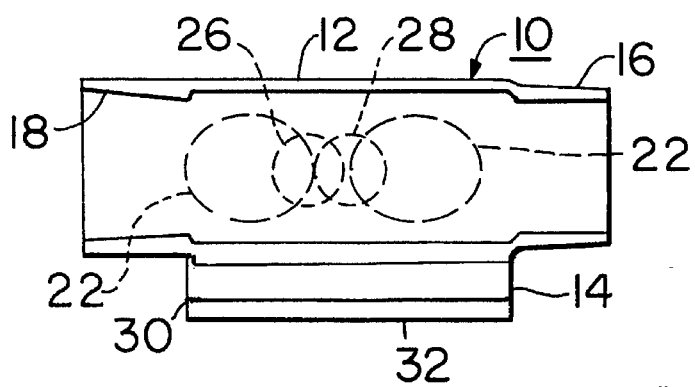
Figure 3:
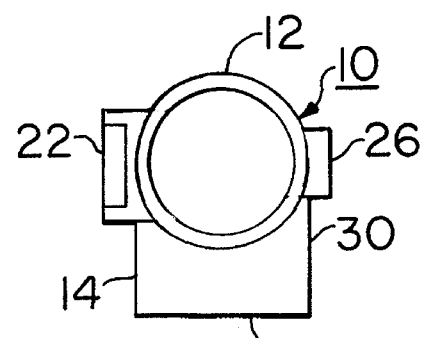

The measuring apparatus 10 has as its main part a respiratory tube 12 of light transmitting, medicinal quality polymer. On the respiratory tube 12 standard connections 16 and 18 are molded, which on the one hand render possible simple plugging to a mask or to a tube and on the other hand simple plugging to a hose connection. The respiratory tube 12 is able to be plug-connected to a housing 14, which contains a pre-amplifier electronic system (not illustrated herein). When plugging the respiratory tube 12 onto the housing of the pre-amplifier electronic system 14 the necessary power supply lines and data lines are joined together with the aid of an encoded plug board.

As more particularly depicted in FIG. 1, opposite tubular heads 20 are formed on the respiratory tube 12 so as to be oblique in relation to the middle axis of the respiratory tube, such heads defining the measurement volume for ultrasonic sensors 22 arranged at the ends of the tubular heads or humps 20. The ultrasonic sensors 22 are accordingly cast into the respiratory tube 12. They are replaced with the same. Further humps or heads 24, also tubular, which are arranged obliquely in relation to the middle axis of the respiratory tube 12 so as to be opposite to one another, define the measurement volume for an infrared light source 26 and an associated optical sensor 28. The measurement volumes of the ultrasonic sensors 22 and the infrared light source 26 and furthermore of the optical sensor 28 intersect with each other, as shown in FIG. 1. Owing to this arrangement of the sensors a particularly compact arrangement is possible.

A pressure transducer 30 is integrated in the wall of the respiratory tube 12 in addition. Furthermore a light source 32 is arranged in the housing. Opposite to the light source 32 a fluorescent layer is applied internally to the respiratory tube in a manner not illustrated.

The signals produced by the measuring apparatus are the result of readings taken simultaneously and without delay in the main flow. This renders possible a particularly simple evaluation, synchronously with respiration, of ventilation and gas exchange of the patient. More particularly, it is possible for respiratory volumes, respiratory frequency, oxygen uptake, release of $CO_2$ and the concentration of anesthetic gases to be determined, A further point is that using a washout method the functional reserve capacity (FRC) of the patient may be determined. The readings obtained and the derived, calculated values are of high accuracy, the technical involvement and expense by substantially less than in measuring equipment mentioned supra. The dead space, which plays an important role in measurements performed with the above mentioned equipment, is minimized.

The device is disposed off after use on one patient so that dangerous cross infections between different patients can be effectively prevented. For special applications the respiratory tube may also be gas sterilized.

We claim:

1. An apparatus for simultaneously measuring respiratory gas parameters comprising a respiratory tube and ultrasonic sensors and preamplifier electronic circuitry which is arranged in a housing separate from the respiratory tube, said ultrasonic sensors are embedded within tubular heads formed on the respiratory tube so that they constitute a single part therewith and wherein at least the respiratory tube with the embedded ultrasonic sensors is designed to form a disposable part for use only once; said apparatus further comprising a pressure sensor integrated in the respiratory tube, wherein the pressure sensor is cast in the respiratory tube.

2. The apparatus as claimed in claim 1, further comprising an infrared light source and opposite thereto an optical sensor wherein the infrared light source and the optical sensor are integrated with the respiratory tube.

3. The apparatus according to claim 2 wherein the respiratory tube is manufactured from a material transparent to light.

4. The apparatus according to claim 3, wherein the respiratory tube is manufactured from a light transmitting medicinal quality polymer.

5. The apparatus according to claim 2, wherein the infrared light source and the optical sensor are cast in a wall of the respiratory tube.

6. The apparatus as claims in claim 2, wherein the infrared light source and the optical sensor are installed adjacent to the ultrasonic sensors transversely along the respiratory tube such that connecting lines between the ultrasonic sensors and connecting lines between the infrared light source and the optical sensor intersect with each other.

7. The apparatus as claims in claim 2, wherein the infrared light source and the optical sensor are adapted to be mounted in position on the respiratory tube using a plug-on holder.

8. The apparatus as claimed in claim 2, wherein the infrared light source and the optical sensor are arranged adjacent to each other, and wherein a wall opposite to the optical sensor is given a mirror finish and is so configured that light emitted from the infrared light source is reflected and is received by the optical sensor.

9. The apparatus as claimed in claim 1, further comprising a light source installed in an electronic circuitry housing to emit suitable light such that light passes through a wall of the respiratory tube and impinges on a suitable fluorescent dye applied thereon and in that adjacent to the light source in the electronic circuitry housing an optical pickup is arranged which is adapted to determine oxygen concentration by luminescence or fluorescence measurements.

10. The apparatus as claimed in claim 1, wherein the housing for the pre-amplifier electronic circuitry is adapted to be flange mounted on the respiratory tube, the conduction of a power supply and of signals to sensors integrated in the respiratory tube and in a reverse direction taking place via an encoded plug-in board.

11. The apparatus as claimed in claim 1, further comprising connections in the housing of the pre-amplifier electronic circuitry for data lines for data representing readings from a separately connected $O_2$ analyzer.

12. The apparatus as claimed in claim 1, wherein the pre-amplifier electronic circuitry is directly cast in a floor of the respiratory tube.

13. An apparatus for simultaneously measuring respiratory gas parameters comprising a respiratory tube and ultrasonic sensors and preamplifier electronic circuitry which is arranged in a housing separate from the respiratory tube, said ultrasonic sensors are embedded within tubular heads formed on the respiratory tube so that they constitute a single part therewith, said apparatus further comprising an infrared light source and opposite thereto an optical sensor wherein said infrared light source and optical sensor are integrated with the respiratory tube, and wherein at least the respiratory tube with the embedded ultrasonic sensors is designed to form a disposable part for use only once; said apparatus further comprising an infrared light source and opposite thereto an optical sensor wherein the infrared light source and the optical sensor are integrated with the respiratory tube, wherein the infrared light source and the optical sensor are cast in a wall of the respiratory tube.

* * * * *